United States Patent
van Vliet et al.

(10) Patent No.: US 11,634,643 B2
(45) Date of Patent: *Apr. 25, 2023

(54) WETTING AND ANTI-FOAMING AGENT

(71) Applicant: Elementis Specialties, Inc., East Windsor, NJ (US)

(72) Inventors: Bart van Vliet, Delden (NL); James A. Heck, Robbinsville, NJ (US); Eduardus Maria Mangnus, Deventer (NL); Chitra Jeurkar, Morganville, NJ (US); Jelle de Vries, Delden (NL); Alart Mulder, Delden (NL)

(73) Assignee: ELEMENTIS SPECIALTIES, INC., East Windsor, NJ (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/341,895

(22) Filed: Jun. 8, 2021

(65) Prior Publication Data
US 2021/0291132 A1  Sep. 23, 2021

Related U.S. Application Data

(63) Continuation of application No. 16/018,552, filed on Jun. 26, 2018, now Pat. No. 11,052,361, which is a continuation of application No. 15/287,852, filed on Oct. 7, 2016, now Pat. No. 10,022,691.

(60) Provisional application No. 62/238,260, filed on Oct. 7, 2015.

(51) Int. Cl.
| | |
|---|---|
| C09K 23/00 | (2022.01) |
| C07C 43/315 | (2006.01) |
| C08G 65/26 | (2006.01) |
| C09D 5/02 | (2006.01) |
| C09D 7/65 | (2018.01) |
| C09D 7/47 | (2018.01) |
| B01D 19/04 | (2006.01) |
| C07C 43/11 | (2006.01) |
| C08G 65/00 | (2006.01) |
| C09D 15/00 | (2006.01) |
| C09D 17/00 | (2006.01) |
| C09D 133/02 | (2006.01) |
| C09D 163/00 | (2006.01) |
| C09D 171/00 | (2006.01) |

(52) U.S. Cl.
CPC .......... *C09K 23/00* (2022.01); *B01D 19/0404* (2013.01); *C07C 43/11* (2013.01); *C07C 43/315* (2013.01); *C08G 65/00* (2013.01); *C08G 65/2609* (2013.01); *C09D 5/024* (2013.01); *C09D 7/47* (2018.01); *C09D 7/65* (2018.01); *C09D 15/00* (2013.01); *C09D 17/002* (2013.01); *C09D 17/008* (2013.01); *C09D 133/02* (2013.01); *C09D 163/00* (2013.01); *C09D 171/00* (2013.01); *C08L 2201/54* (2013.01)

(58) Field of Classification Search
None
See application file for complete search history.

(56) References Cited

U.S. PATENT DOCUMENTS

| | | |
|---|---|---|
| 4,418,217 A | 11/1983 | Schmid et al. |
| 5,403,508 A | 4/1995 | Reng et al. |
| 5,456,847 A | 10/1995 | Guth et al. |
| 5,484,540 A | 1/1996 | Hubesch |
| 5,484,553 A | 1/1996 | Guth et al. |
| 5,501,815 A | 3/1996 | Man |
| 5,501,817 A | 3/1996 | Kischkel et al. |
| 5,516,451 A | 5/1996 | Schmitt et al. |
| 5,516,452 A | 5/1996 | Welch et al. |
| 5,518,648 A | 5/1996 | Welch et al. |

(Continued)

FOREIGN PATENT DOCUMENTS

| | | |
|---|---|---|
| WO | 2012036700 A1 | 3/2012 |
| WO | 2014088124 A1 | 6/2014 |

(Continued)

OTHER PUBLICATIONS

Extended European Search Report dated Jun. 15, 2021, issued in corresponding EP Application No. 21159946.9-1107.
Technical Examination Report dated Jun. 4, 2021, issued in corresponding Brazilian Application No. BR112018006311-8.
First Office Action for corresponding Chinese application No. 201680057076.5 dated Aug. 13, 2020, 17 pages.
English translation of "The preparation and performance study of a kind of polyether polyols for high-activity surfactant", Wei Xu, Proceedings of the 16th Annual Meeting of China Polyurethane Industry Association, pp. 214-217, published Oct. 31, 2014.

(Continued)

*Primary Examiner* — Yun Qian
(74) *Attorney, Agent, or Firm* — Carol A. Marmo; Eckert Seamans Cherin & Mellott, LLC

(57) ABSTRACT

A wetting agent according to Formula (I):

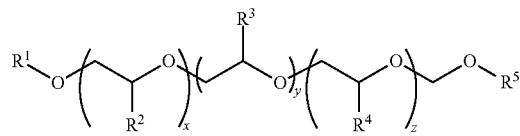

wherein $R^1$ is selected from a branched alkyl group or linear alkyl group or a cycloaliphatic group or an aromatic group, each having 6 to 15 carbon atoms; $R^2$ is selected from hydrogen, methyl, or ethyl; $R^3$ is selected from hydrogen, methyl, or ethyl; $R^4$ is selected from hydrogen, methyl, or ethyl; $R^5$ is selected from methyl or ethyl; x ranges from 0 to 5; y ranges from 0 to 10; z ranges from 1 to 10; with the proviso that when x ranges from 1 to 5, $R^2$ is different from $R^3$; and with the proviso that when x=0, $R^3$ is different from $R^4$. The wetting agent also imparts anti-foam properties to aqueous solutions while reducing surface tension.

8 Claims, 1 Drawing Sheet

(56) References Cited

U.S. PATENT DOCUMENTS

| | | | |
|---|---|---|---|
| 5,536,884 | A | 7/1996 | Stoeckigt et al. |
| 5,545,347 | A | 8/1996 | Ouyang et al. |
| 5,589,099 | A | 12/1996 | Baum |
| 5,612,305 | A | 3/1997 | Lewis |
| 5,661,121 | A | 8/1997 | Dahlgren et al. |
| 5,691,299 | A | 11/1997 | Fabry |
| 5,705,476 | A | 1/1998 | Hoffarth |
| 5,731,132 | A | 3/1998 | Van Werden et al. |
| 5,801,135 | A | 9/1998 | Miyauchi et al. |
| 5,821,213 | A | 10/1998 | Burke et al. |
| 5,827,453 | A | 10/1998 | Gross et al. |
| 5,843,880 | A | 12/1998 | Mertens |
| 5,847,229 | A | 12/1998 | Bigorra Llosas et al. |
| 5,858,117 | A | 1/1999 | Oakes et al. |
| 5,858,279 | A | 1/1999 | Lunski et al. |
| 5,861,366 | A | 1/1999 | Ihns et al. |
| 5,866,530 | A | 2/1999 | Schmid et al. |
| 5,876,514 | A | 3/1999 | Rolando et al. |
| 5,877,245 | A | 3/1999 | Wiggins et al. |
| 5,895,605 | A | 4/1999 | Gross et al. |
| 5,929,012 | A | 7/1999 | Del Duca et al. |
| 5,929,014 | A | 7/1999 | Beaujean et al. |
| 5,935,919 | A | 8/1999 | Shinomiya et al. |
| 5,935,920 | A | 8/1999 | Geke et al. |
| 5,981,462 | A | 11/1999 | Mertens |
| 5,985,820 | A | 11/1999 | Khan-Lodhi et al. |
| 5,986,122 | A | 11/1999 | Lewis et al. |
| 6,001,790 | A * | 12/1999 | Schmitt ........ C11D 1/8355 510/423 |
| 6,015,781 | A | 1/2000 | Vinson et al. |
| 6,025,318 | A | 2/2000 | Mertens |
| 6,028,229 | A | 2/2000 | Bigorra Llosas et al. |
| 6,080,716 | A | 6/2000 | Skoeld et al. |
| 6,093,856 | A | 7/2000 | Cripe et al. |
| 6,110,977 | A | 8/2000 | Gross et al. |
| 6,133,211 | A | 10/2000 | Cobianco et al. |
| 6,133,222 | A | 10/2000 | Vinson et al. |
| 6,136,773 | A | 10/2000 | Mertens |
| 6,153,577 | A | 11/2000 | Cripe et al. |
| 6,187,739 | B1 | 2/2001 | Merz et al. |
| 6,197,739 | B1 | 3/2001 | Oakes et al. |
| 6,204,233 | B1 | 3/2001 | Smith et al. |
| 6,228,829 | B1 | 5/2001 | Vinson et al. |
| 6,242,389 | B1 | 6/2001 | Elliott et al. |
| 6,268,327 | B1 | 7/2001 | Lu et al. |
| 6,271,191 | B1 | 8/2001 | Kerobo et al. |
| 6,274,756 | B1 | 8/2001 | Caers |
| 6,277,801 | B1 | 8/2001 | Dahanayake et al. |
| 6,281,181 | B1 | 8/2001 | Vinson et al. |
| 6,326,348 | B1 | 12/2001 | Vinson et al. |
| 6,329,333 | B1 | 12/2001 | Merz et al. |
| 6,335,311 | B1 | 1/2002 | Namiki et al. |
| 6,342,474 | B1 | 1/2002 | Kerobo et al. |
| 6,362,259 | B1 | 3/2002 | Natale et al. |
| 6,387,962 | B1 | 5/2002 | Wiggins et al. |
| 6,399,556 | B2 | 6/2002 | Smith et al. |
| 6,472,440 | B2 | 10/2002 | Gross et al. |
| 6,506,945 | B2 | 1/2003 | Kluesener et al. |
| 6,532,973 | B1 | 3/2003 | Gross et al. |
| 6,566,317 | B2 | 5/2003 | Morris et al. |
| 6,583,185 | B2 | 6/2003 | Wiggins et al. |
| 6,620,774 | B1 | 9/2003 | Del Duca et al. |
| 6,680,286 | B1 | 1/2004 | Kawaguchi et al. |
| 6,683,035 | B1 | 1/2004 | Koester et al. |
| 6,686,330 | B2 | 2/2004 | Jordan, IV et al. |
| 6,693,065 | B2 | 2/2004 | Gentilhomme et al. |
| 6,730,239 | B1 | 5/2004 | Kanno et al. |
| 6,797,687 | B2 | 9/2004 | Kischkel et al. |
| 6,821,942 | B2 | 11/2004 | Sebillotte-Arnaud et al. |
| 6,835,703 | B1 | 12/2004 | Cho et al. |
| 6,851,433 | B1 | 2/2005 | Gross et al. |
| 6,892,739 | B2 | 5/2005 | Merz et al. |
| 6,903,066 | B2 | 6/2005 | Kischkel et al. |
| 7,012,052 | B1 | 3/2006 | Kluesener et al. |
| 7,018,963 | B2 | 3/2006 | Mizusaki et al. |
| 7,084,101 | B2 | 8/2006 | Kerobo et al. |
| 7,105,706 | B2 | 9/2006 | Dirkzwager et al. |
| 7,115,779 | B2 | 10/2006 | Ohtawa et al. |
| 7,268,259 | B1 | 9/2007 | Behler et al. |
| 7,297,671 | B2 | 11/2007 | Thankachan et al. |
| 7,297,674 | B2 | 11/2007 | Hines |
| 7,332,466 | B2 | 2/2008 | Schmid et al. |
| 7,335,235 | B2 | 2/2008 | Ruland et al. |
| 7,361,708 | B2 | 4/2008 | Hashi et al. |
| 7,371,716 | B2 | 5/2008 | Ruland et al. |
| 7,544,650 | B2 | 6/2009 | Thankachan et al. |
| 7,557,074 | B2 | 7/2009 | Becker et al. |
| 7,563,759 | B2 | 7/2009 | Rogmann et al. |
| 7,608,576 | B2 | 10/2009 | Company et al. |
| 7,776,158 | B2 | 8/2010 | Rogmann et al. |
| 7,834,084 | B2 | 11/2010 | Tsuda et al. |
| 7,863,234 | B2 | 1/2011 | Maki et al. |
| 7,871,971 | B1 | 1/2011 | Koester et al. |
| 7,981,854 | B2 | 7/2011 | Fuji et al. |
| 8,048,842 | B2 | 11/2011 | Doi et al. |
| 8,063,009 | B2 | 11/2011 | Onoda et al. |
| 8,114,827 | B2 | 2/2012 | Shamayeli et al. |
| 8,119,717 | B2 | 2/2012 | Anchor et al. |
| 8,172,953 | B2 | 5/2012 | Hodge et al. |
| 8,178,117 | B2 | 5/2012 | Taranta et al. |
| 8,314,057 | B2 | 11/2012 | Christensen et al. |
| 8,334,323 | B2 | 12/2012 | Varineau et al. |
| 8,357,823 | B2 | 1/2013 | Wurm et al. |
| 8,431,639 | B2 | 4/2013 | Anchor |
| 8,546,306 | B2 | 10/2013 | Levy et al. |
| 8,580,727 | B2 | 11/2013 | Man et al. |
| 8,618,041 | B2 | 12/2013 | Toussaint et al. |
| 8,685,912 | B2 | 4/2014 | Maeyama et al. |
| 8,697,622 | B2 | 4/2014 | Man et al. |
| 8,709,169 | B2 | 4/2014 | Company et al. |
| 8,741,809 | B2 | 6/2014 | Troppmann et al. |
| 8,785,363 | B2 | 7/2014 | Man et al. |
| 8,828,911 | B2 | 9/2014 | Zhu |
| 8,877,681 | B2 | 11/2014 | Berghaus et al. |
| 8,911,560 | B2 | 12/2014 | Perdigon et al. |
| 8,951,573 | B2 | 2/2015 | Suekuni et al. |
| 8,980,818 | B2 | 3/2015 | Wates et al. |
| 8,986,467 | B2 | 3/2015 | Vandermeulen et al. |
| 2002/0072573 | A1 | 6/2002 | Bentley et al. |
| 2003/0027740 | A1 | 2/2003 | Weuthen et al. |
| 2003/0069152 | A1 | 4/2003 | Kim |
| 2003/0092593 | A1 | 5/2003 | Farooq et al. |
| 2003/0196685 | A1 | 10/2003 | Anzures et al. |
| 2004/0110655 | A1 | 6/2004 | Yamashita et al. |
| 2004/0138075 | A1 | 7/2004 | Brown et al. |
| 2004/0157745 | A1 | 8/2004 | Vermeer et al. |
| 2004/0180022 | A1 | 9/2004 | Denzligil |
| 2004/0248759 | A1 | 12/2004 | Smith et al. |
| 2004/0250737 | A1 | 12/2004 | Yaguchi et al. |
| 2004/0266652 | A1 | 12/2004 | Brown et al. |
| 2007/0010411 | A1 | 1/2007 | Amemiya et al. |
| 2007/0261720 | A1 | 11/2007 | Sugerman et al. |
| 2008/0039666 | A1 | 2/2008 | Grothe et al. |
| 2008/0188397 | A1 | 8/2008 | Company et al. |
| 2009/0258983 | A1 | 10/2009 | Fernandez et al. |
| 2009/0286684 | A1 | 11/2009 | Scherl et al. |
| 2009/0305940 | A1 | 12/2009 | Schimmel et al. |
| 2010/0062666 | A1 | 3/2010 | Siemensmeyer et al. |
| 2010/0160165 | A1 | 6/2010 | Bratz et al. |
| 2010/0184603 | A1 | 7/2010 | Stoesser et al. |
| 2011/0039904 | A1 | 2/2011 | Steinbrenner et al. |
| 2011/0212870 | A1 | 9/2011 | Lant |
| 2012/0021914 | A1 | 1/2012 | Berghaus et al. |
| 2012/0172228 | A1 | 7/2012 | Bell |
| 2012/0252712 | A1 | 10/2012 | Albers et al. |
| 2013/0197276 | A1 | 8/2013 | Spiegler et al. |
| 2013/0225471 | A1 | 8/2013 | Taneja et al. |
| 2013/0252982 | A1 | 9/2013 | Busch et al. |
| 2014/0196220 | A1 | 7/2014 | Man et al. |
| 2014/0311529 | A1 | 10/2014 | Nishio et al. |
| 2014/0378309 | A1 | 12/2014 | Zhu |
| 2015/0050232 | A1 | 2/2015 | Zhu et al. |
| 2015/0056156 | A1 | 2/2015 | Zhu et al. |
| 2015/0111803 | A1 | 4/2015 | Liu et al. |

(56) References Cited

U.S. PATENT DOCUMENTS

| | | |
|---|---|---|
| 2015/0126429 A1 | 5/2015 | Thyberg et al. |
| 2015/0147802 A1 | 5/2015 | Nishio |
| 2015/0230457 A1 | 8/2015 | Gandhi et al. |

FOREIGN PATENT DOCUMENTS

| | | |
|---|---|---|
| WO | 2014091363 A1 | 6/2014 |
| WO | 2014095793 A1 | 6/2014 |
| WO | 2014096776 A1 | 6/2014 |
| WO | 2014139653 A2 | 9/2014 |

OTHER PUBLICATIONS

English translation of "Application research of non-APEO surfactants in aqueous architectural coatings", Yuan Ren, China Excellent Master's Thesis Database Engineering Science II Series, Issue 10, pp. 1-2, 14-17, 28-32 and 38-65, published Oct. 15, 2012.

First Examination Report for corresponding Indian Patent Application No. 201817010386 dated May 1, 2020, 5 pages.

Extended European Search Report for corresponding European Application No. 19205834.5 dated Feb. 13, 2020, 5 pages.

Ivanova N A et al: "Wetting dynamics of polyoxyethylene alkyl ethers and trisiloxanes in respect of polyoxyethylene chains and properties of substrates", Colloids and Surfaces a: Physiochemical and Engineering Aspects, vol. 413, May 11, 2012, pp. 307-313.

Examination Report for corresponding Australian Application No. 2016335680 dated Nov. 28, 2019, 2 pages.

N.A. Ivanova et al., "Wetting dynamics of polyoxyethylene alkyl ethers and trisiloxanes in respct of polyoxyethylene chains and properties of substrates", Colloids and Surfaces A: Physiochemical and Engineering Aspects, vol. 413, May 11, 2012, pp. 307-313.

Supplementary European Search Report for corresponding European application No. 16854378.3 dated Apr. 4, 2019, 6 pages.

International Search Report relating to PCT/US2016/055884, dated Feb. 16, 2017.

Written Opinion relating to PCT/US2016/055884, dated Feb. 16, 2017.

International Preliminary Report on Patentability relating to PCT/US2016/055884, dated Apr. 10, 2018.

Office Action issued in U.S. Appl. No. 15/287,852, dated Jul. 6, 2017.

Office Action issued in U.S. Appl. No. 15/287,852, dated Sep. 8, 2017.

* cited by examiner

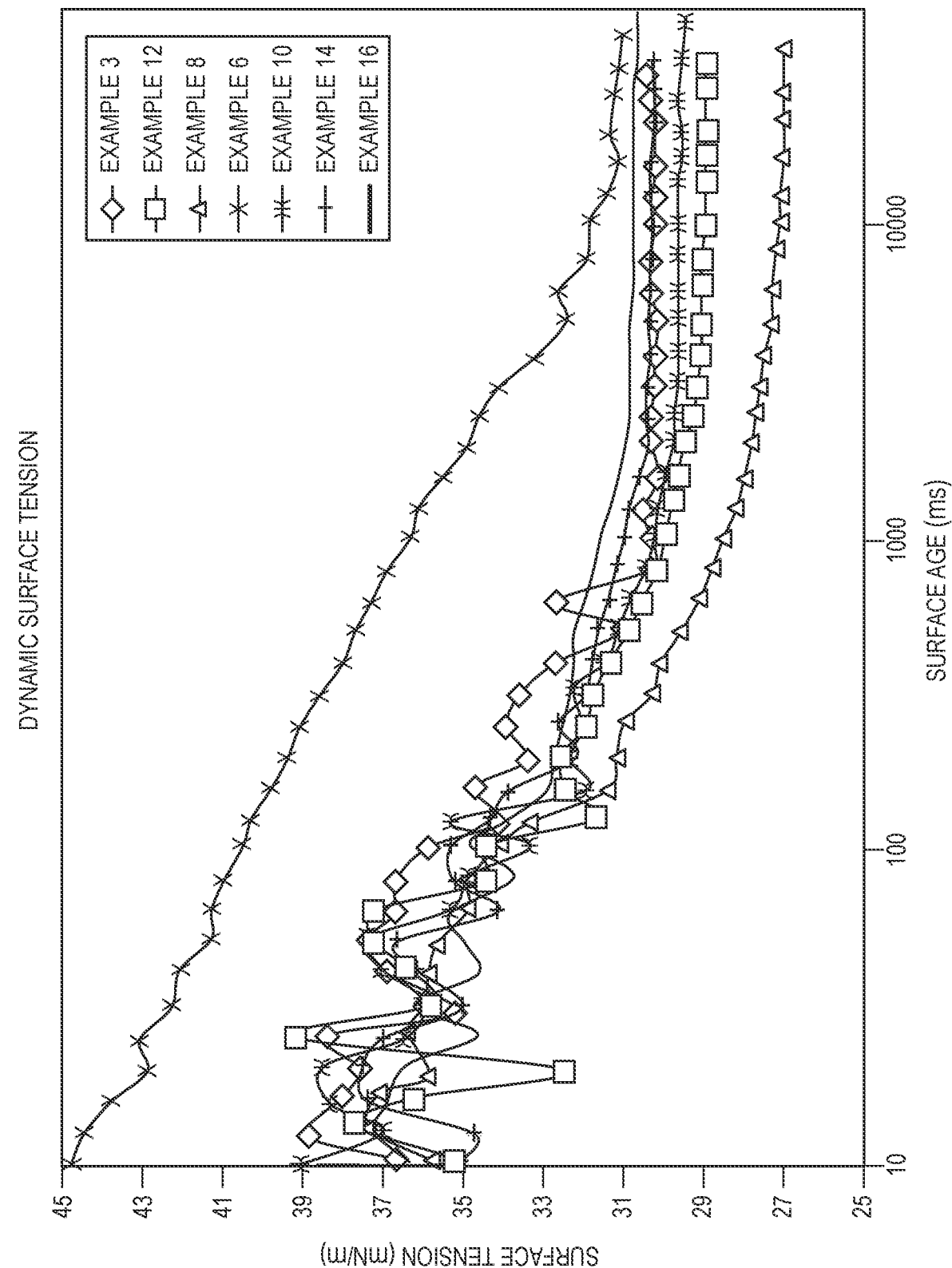

WETTING AND ANTI-FOAMING AGENT

CROSS-REFERENCE TO RELATED APPLICATIONS

This application is a continuation of prior U.S. application Ser. No. 16/018,552, filed Jun. 26, 2018 which is a continuation of prior U.S. application Ser. No. 15/287,852, filed Oct. 7, 2016 (now U.S. Pat. No. 10,022,691), which claims priority benefit from U.S. Provisional Patent Application 62/238,260 filed Oct. 7, 2015, each of which is incorporated by reference herein in its entirety.

FIELD OF THE INVENTION

The present invention relates to use of multifunctional alkoxylate compositions as dual wetting and anti-foaming agents.

BACKGROUND OF INVENTION

The ability to reduce the surface tension of water is important for waterborne coating formulations as decreased surface tension leads to enhanced substrate wetting particularly for hydrophobic surfaces. Static- and dynamic surface tension are important measures of the ability of a wetting agent to reduce surface tension in aqueous systems.

Traditional nonionic surfactants, such as alkylphenol or alkyl ethoxylates and ethylene oxide (EO)/propylene oxide (PO) copolymers, and anionic surfactants, such as sodium dialkyl sulfosuccinates, exhibit acceptable static surface tension properties. However, many of these surfactants create foam, which can lead to surface defects, poor adhesion, and processing difficulties.

SUMMARY OF INVENTION

In an embodiment, the invention provides for a wetting agent comprising a composition according to Formula (I):

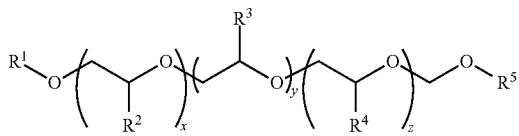

wherein $R^1$ is selected from a branched alkyl group, a linear alkyl group or a cycloaliphatic group or an aromatic group, each having 6 to 15 carbon atoms; $R^2$ is selected from hydrogen, methyl, or ethyl; $R^3$ is selected from hydrogen, methyl, or ethyl; $R^4$ is selected from hydrogen, methyl, or ethyl; $R^5$ is selected from methyl or ethyl; x ranges from 0 to 5; y ranges from 0 to 10; z ranges from 1 to 10; with the proviso that when x ranges from 1 to 5, $R^2$ is different from $R^3$; and with the proviso that when x=0, $R^3$ is different from $R^4$.

In another embodiment, the wetting agent according to Formula (I), further comprising a composition according to Formula (II):

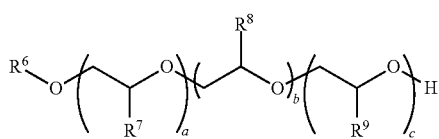

wherein $R^6$ is the same as $R^7$ is the same as $R^2$, $R^8$ is the same as $R^3$ and $R^9$ is the same as $R^4$, a equals x, b equals y and c equals z.

In one embodiment of the wetting agent according to Formula (I), $R^1$ is selected from a branched alkyl group or linear alkyl group or a cycloaliphatic group or an aromatic group, each having 6 to 10 carbon atoms.

In one embodiment of the wetting agent according to Formula (I), $R^1$ is selected from nonyl, iso-nonyl, 3,5,5-trimethyl hexyl, octyl, 2-methyl heptyl, 2-ethyl hexyl, 2,2,4-trimethyl pentyl, 4-methyl pentyl, heptyl, hexyl and combinations thereof. In one such embodiment, x is zero, y ranges from 2 to 5, z ranges from 3 to 10, $R^3$ is hydrogen or methyl and $R^4$ is hydrogen or methyl.

In various embodiments, a 0.3 wt. % solution of the wetting agent composition in deionized water has a measured dynamic surface tension ranging from: 50 mN/m to 25 mN/m; 45 mN/m to 25 mN/m; 40 mN/m to 25 mN/m; or 35 mN/m to 25 mN/m each at a surface age of 1000 ms or less.

In other various embodiment, a 0.3 wt. % solution of the wetting agent composition in deionized water has a measured dynamic surface tension ranging from: 50 mN/m to 25 mN/m; 45 mN/m to 25 mN/m; 40 mN/m to 25 mN/m; or 35 mN/m to 25 mN/m each at a surface age of 30,000 ms.

In other various embodiments, a 0.3 wt. % solution of the wetting agent in deionized water has a static surface tension ranging from: 45 mN/m to 25 mN/m; 40 mN/m to 25 mN/m; or 35 mN/m to 25 mN/m.

The present invention further provide an embodiment for a method for defoaming and/or for preventing foaming of liquid media, comprising mixing the an embodiment of wetting agents described herein, an emulsion thereof, or a powder thereof, with the liquid media.

BRIEF DESCRIPTION OF THE DRAWINGS

The foregoing summary, as well as the following detailed description of the invention, will be better understood when read in conjunction with the appended drawings.

The FIGURE illustrates a plot of surface age versus surface tension for various inventive compositions described herein.

DETAILED DESCRIPTION OF THE EMBODIMENTS

The present disclosure provides for a dual wetting and anti-foam agent.

In an embodiment, the invention provides for a wetting agent comprising a composition according to Formula (I):

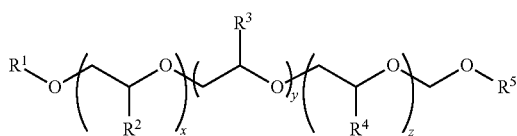

wherein $R^1$ is selected from a branched alkyl group, a linear alkyl group or a cycloaliphatic group or an aromatic group, each having 6 to 15 carbon atoms; $R^2$ is selected from hydrogen, methyl, or ethyl; $R^3$ is selected from hydrogen, methyl, or ethyl; $R^4$ is selected from hydrogen, methyl, or ethyl; $R^5$ is selected from methyl or ethyl; x ranges from 0 to 5; y ranges from 0 to 10; z ranges from 1 to 10; with the proviso that when x ranges from 1 to 5, $R^2$ is different from $R^3$; and with the proviso that when x=0, $R^3$ is different from $R^4$.

In another embodiment, the wetting agent according to Formula (I), further comprising a composition according to Formula (II):

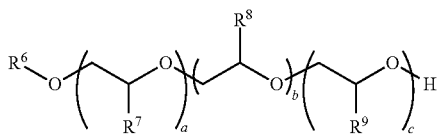

wherein $R^6$ is the same as $R^7$ is the same as $R^2$, $R^8$ is the same as $R^3$ and $R^9$ is the same as $R^4$, a equals x, b equals y and c equals z.

In such embodiments, wetting agents comprising compositions according to Formula I and Formula II that may contain varying amounts of such compounds according to: 50 wt. % Formula I and 50 wt. % Formula II; 60 wt. % Formula I and 40 wt. % Formula II; 75 wt. % Formula I and 25 wt. % Formula II; 85 wt. % Formula I and 15 wt. % Formula II; 95 wt. % Formula I and 5 wt. % Formula II.

In some other embodiments, wetting agents comprising compositions according Formula (I) and Formula (II) may contain varying amounts of such compounds according to: 50 wt. %-99 wt. % Formula I and 1 wt. % to 50 wt. % Formula II; 60 wt. %-99 wt. % Formula I and 1 wt. % to 40 wt. % Formula II; 70 wt. %-99 wt. % Formula I and 1 wt. % to 30 wt. % Formula II; 80 wt. %-99 wt. % Formula I and 1 wt. % to 20 wt. % Formula II; 90 wt. %-99 wt. % Formula I and 1 wt. % to 10 wt. % Formula II; 95 wt. %-99 wt. % Formula I and 1 wt. % to 5 wt. % Formula II.

In one embodiment of the wetting agent according to Formula (I), $R^1$ is selected from a branched alkyl group or linear alkyl group or a cycloaliphatic group or an aromatic group, each having 6 to 10 carbon atoms.

In one embodiment of the wetting agent according to Formula (I), $R^1$ is selected from nonyl, iso-nonyl, 3,5,5-trimethyl hexyl, octyl, 2-methyl heptyl, 2-ethyl hexyl, 2,2,4-trimethyl pentyl, 4-methyl pentyl, heptyl, hexyl and combinations thereof. In one such embodiment, x is zero, y ranges from 2 to 5, z ranges from 3 to 10, $R^3$ is hydrogen or methyl and $R^4$ is hydrogen or methyl.

In embodiments of the foregoing wetting agents, a 0.3 wt. % solution of the wetting agent composition in deionized water has a measured dynamic surface tension ranging from: 50 mN/m to 25 mN/m; 45 mN/m to 25 mN/m; 40 mN/m to 25 mN/m; or 35 mN/m to 25 mN/m each at a surface age of 1000 ms or less.

In other embodiments of the foregoing wetting agents, a 0.3 wt. % solution of the wetting agent composition in deionized water has a measured dynamic surface tension ranging from: 50 mN/m to 25 mN/m; 45 mN/m to 25 mN/m; 40 mN/m to 25 mN/m; or 35 mN/m to 25 mN/m each at a surface age of 30,000 ms.

In other embodiments of the foregoing wetting agents, a 0.3 wt. % solution of the wetting agent in deionized water has a static surface tension ranging from: 45 mN/m to 25 mN/m; 40 mN/m to 25 mN/m; or 35 mN/m to 25 mN/m.

In embodiments of the foregoing wetting agents, a 0.3 wt. % solution of the wetting agent in aqueous solution has a foaming value less than 17 cm when measured at a concentration of 0.3 wt. % according to the foam test procedure described herein, and has a foaming value less than 3 cm when measured at a concentration of 0.3 wt. %, at 5 minutes after completion of the foam test procedure. In another embodiment, the present invention provides for an aqueous composition comprising an effective amount of any of the foregoing wetting agents in deionized water wherein the wetting agent also acts as an anti-foam agent. In embodiments of the aqueous composition, an effective amount of any of the foregoing wetting agents ranges from: 0.01 wt. % to 7.0 wt. %; 0.1 wt. % to 5.0 wt. %; 0.1 wt. % to 3.0 wt. %; 0.1 wt. % to 1.0 wt. %; and 0.1 wt. % to 0.5 wt. %.

In one such embodiment, the aqueous composition has a foaming value less than 17 cm when measured at a concentration of 0.3 wt. % according to the foam test procedure, described herein, and has a foaming value less than 3 cm when measured at a concentration of 0.3 wt. % 5 minutes after completion of the foam test procedure. In another such embodiment, the aqueous composition has a foaming value less than 10 cm when measured at a concentration of 0.3 wt. % according to the foam test procedure, described herein, and has a foaming value less than 1 cm when measured at a concentration of 0.3 wt. %, at 5 minutes after completion of the foam test procedure. In yet another such embodiment, the aqueous composition has a foaming value less than 5 cm when measured at a concentration of 0.3 wt. % according to the foam test procedure, described herein, and has a foaming value less than 1 cm when measured at a concentration of 0.3 wt. %, at 5 minutes after completion of the foam test procedure. In still yet another such embodiment, the aqueous composition has a foaming value less than 2 cm when measured at a concentration of 0.3 wt. % according to the foam test procedure, described herein, and has a foaming value less than 1 cm when measured at a concentration of 0.3 wt. %, at 5 minutes after completion of the foam test procedure. In a particular such embodiment, the aqueous composition has a foaming value of 0 cm when measured at a concentration of 0.3 wt. % according to the foam test procedure, described herein, and has a foaming value of 0 cm when measured at a concentration of 0.3 wt. %, at 5 minutes after completion of the foam test procedure.

Each of the foregoing embodiments of aqueous composition wherein the wetting agent also acts as an anti-foam agent, the wetting agent also provides static tension control. In some such embodiments, a 0.3 wt. % solution of the wetting agent composition in deionized water has a measured dynamic surface tension ranging from: 50 mN/m to 25 mN/m; 45 mN/m to 25 mN/m; 40 mN/m to 25 mN/m; or 35 mN/m to 25 mN/m each at a surface age of 1000 ms or less. In other such embodiments, a 0.3 wt. % solution of the wetting agent composition in deionized water has a measured dynamic surface tension ranging from: 50 mN/m to 25 mN/m; 45 mN/m to 25 mN/m; 40 mN/m to 25 mN/m; or 35 mN/m to 25 mN/m each at a surface age of 30,000 ms. In still other embodiments, a 0.3 wt. % solution of the wetting agent in deionized water has a static surface tension ranging from: 45 mN/m to 25 mN/m; 40 mN/m to 25 mN/m; or 35 mN/m to 25 mN/m. In other embodiments of the foregoing aqueous compositions, the aqueous composition comprises a latex polymer. In other embodiments of the foregoing aqueous compositions, the aqueous composition comprises a pigment.

In other embodiments of the foregoing aqueous compositions, the foregoing embodiments of wetting agents may be used with polymeric binder which may be either solvent or water borne. Waterborne binder is typically in the form of discrete solid polymeric particles formed by the polymerization of at least one ethylenically-unsaturated monomer in an aqueous dispersion medium. The polymeric particles are typically formed by emulsion polymerization in accordance with known technology.

Representative polymeric particles that are suitable for the aqueous composition include acrylic polymers, vinyl acetate polymers, vinyl chloride polymers, acrylic urethanes, water reducible alkyds, alkyd emulsions, styrene acrylic, VAE and combinations thereof. Suitable acrylic polymers include copolymers of acrylonitrile, acrylic acid, methacrylic acid, butylacrylic acid, butyl acrylates, ethyl acrylates, methyl methacrylate, vinyl acetate, styrene, and combinations thereof.

In another embodiment of the foregoing aqueous compositions, the foregoing embodiments of wetting agents may be used in aqueous composition comprising a pigment which may be either organic or inorganic. A wide range of pigments may be included in the composition. Suitable pigments include inorganic pigments such as titanium dioxide, pigmentary iron oxide ($Fe_2O_3$) and organic pigments including blue pigments, green pigments, yellow pigments arylide yellow, Hansa® Bright yellow, red pigments, quinacridone red, violet pigments, orange pigments and similar materials.

In another embodiment of the foregoing aqueous compositions, the foregoing embodiments of wetting agent may be used in coating which may be either solvent or waterborne. For example, water borne coating may include adhesion promoters, rheology modifiers, dispersing agents, defoamers, biocides, fillers, pH control additives, open time extenders, and polymer which is typically a water-based latex component, and the coating composition may be referred to as "latex-based" paint.

In other embodiments of the foregoing wetting agent, the wetting agent may be used in water based, solvent based, or solvent free formulations for industrial coatings, automotive coatings, adhesives, and sealant applications for the purposes of facilitating substrate wetting, pigment wetting by the resin or solvent, and improving compatibility multiphase compositions in such as an epoxy containing rubber particles. Examples of adhesives and sealant resin types include epoxy, polyurethane, acrylic, MS Polymer™, SPUR polymer, styrene-budiene, styrene-phenolic, polylactic acid, polyaspartic acid, ethylene propylene diene terpolymer (EPDM), polysiloxane, polyurea, cementitious, and also hybrid combinations of the resins such as epoxy-silane coating products.

In other embodiments of the foregoing wetting agent, the wetting agent may be used in powder coatings for the purposes of facilitating substrate wetting, pigment wetting by the resin or solvent, and improving compatibility multiphase compositions in such as an epoxy formulation also containing a urethane resin. Examples of powder coating resins include acrylic, polyester, epoxy, polyanhydride, unsaturated resins for UV curing, glycoluril, and hybrids combinations such as acrylic-epoxy products.

In another embodiment, the invention provides for a method for defoaming and/or for preventing foaming of liquid media by mixing the liquid medium with any of the foregoing embodiments of the wetting agent described herein, an emulsion thereof, or a powder thereof. In some such embodiments, the liquid media comprises a latex polymer. In other such embodiments, the liquid media comprises a pigment.

The various embodiments of wetting agents, described herein, may be prepared in a sequential manner. In one example, the wetting agent may be prepared by a first propoxylation step where oxypropylene moieties ("PO") are attached to an alcohol or mixture of alcohols to form a PO block. After the propoxylation step, oxyethylene moieties ("EO") are added to form an EO block attached to the PO block. Subsequent to the ethoxylation step, an organic moiety is added as an end group. Organic moieties include trimethysilyl and trifluoromethyl and similar. In another example, the wetting agent may be prepared by a first ethoxylation step where oxyethylene moieties ("EO") are attached an alcohol or mixture of alcohols to form an EO block. After the ethoxylation step, oxypropylene moieties ("PO") are added to form a PO block attached to the EO block. Subsequent to the propoxylation step, an organic moiety is added as an end group. In another example, the wetting agent may be prepared by a first ethoxylation step where oxyethylene moieties ("EO") are attached an alcohol or mixture of alcohols to form an EO block. After the ethoxylation step, oxypropylene moieties ("PO") are added to form a PO block attached to the EO block. After the propoxylation step, oxyethylene moieties ("EO") are added to form an EO block attached to the PO block. Subsequent to the ethoxylation step, an organic moiety is added as end group. In preceding examples individual oxypropylene moieties ("PO") can be exchanged for oxybutylene moieties ("BO") to form a BO block. This method can be used to make all possible permutations as described in Formula I and Formula II.

Description of Test Methods

A variety of methods may be used to characterize the physical properties of exemplary wetting agent compositions and aqueous compositions. The methods are described below.

Wetting Agent Aqueous Solution Evaluation
Foam Test Procedure

In a clean glass container, 0.3 grams of wetting agent and 99.70 grams of deionized water were mixed for two minutes and then 50 mL of the mixture was poured in a 250 mL graduated cylinder. A clean air bubble diffuser stone (Penn Plax Air Stone, 7/16" Cylinder, Model AS6B) was attached to rubber tubing that was attached to a Maxima air pump model #A-805 which supplies air at 2.5 psi with a flow rate: 2300-2500 cc/min. This is the actual flow rate with the diffuser stone in place and submerged in 50 mL of 0.3 wt. % wetting agent in deionized water. The air bubble diffuser stone was placed in the graduated cylinder filled with the aqueous solution. Air is pumped into the aqueous solution for 30 seconds or in case of foaming solutions at a reduced time until the height reaches 250 ml. The air supply is then stopped.

The height of the bubbling solution is recorded immediately after removing air source and at set time intervals until solution height returns to 50 ml or stabilizes. For the foam test procedure, the 200 mL mark, of a 250 mL graduated cylinder, equals 17 cm±0.2 cm.

Surface Tension Reduction

Static Surface Tension (SST) may be measured by someone skilled in the art, with a surface tensiometer (i.e. Kruss™ K100 Tensiometer) using the Wilhelmy Plate method. Static Surface Tension (SST) measurements demonstrate the lowest surface tension that a wetting agent can achieve in solution independent of kinetic mobility restrictions that particular surfactants may have. This is an indicator of the surface tension reducing capability of a wetting agent. The Wilhelmy Plate method for evaluating SST is a well-established method in the industry and was used to measure the surface tension produced by the wetting agents described herein.

Dynamic Surface Tension (DST) may be measured by someone skilled in the art with a bubble tensiometer (i.e. Kruss™ BP2 Bubble Tensiometer). Dynamic surface tension (DST) measurements allow for the assessment of a wetting agent's intrinsic ability to reduce interfacial surface tension. DST measures the surface tension of aqueous solutions of the wetting agent over a range of surface ages generated by bubbling gas into the solutions at different rates. By varying the rate of bubbling, different ages of bubble surfaces are created, and the instrument determines the surface tension at each of these different rates and reveals intrinsic kinetic mobility restrictions that particular wetting agents may have. Kinetic mobility restrictions can limit a wetting agent's wetting performance when the application speed exceeds the mobility limits of the wetting agent. Short surface ages (10 ms) relate to rapid droplet formation which might occur during spray atomization. Long surface ages (30,000-50,000 ms) may relate closer to brushing type coating applications and levelling. This technique generates a characteristic curve profile for a wetting agent over the range of surface ages in the test.

Water Droplet Spreading

Plastic panels were used as substrates for depositing the aqueous solutions. The panels were 4"×6" (95 mm×145 mm) Dow Pulse 2000 black PC/ABS panels. The glossy side was wiped with IPA using a paper towel and allowed to air dry. Solutions of each of wetting agent were prepared ahead of time at 0.3% concentration by weight in deionized water. A blank solution containing only deionized water was tested as a baseline reference.

The deposition of the aqueous solutions on the panels was performed as follows: A separate panel was used for each tested solution. Syringes with attached needles were used to deposit the solutions (B-D 1 cc 25G ⅝ Tuberculin Syringe & Precision Glide Needle—Part 9626). The solutions were drawn up in the syringe until they contained precisely 1.0 ml of the solution. The syringe was placed vertically in the center of the test panel on the bench, with the syringe tip oriented perpendicularly and placed in direct contact resting on the surface of the panel. The plunger was steadily pressed down and the liquid was deposited slowly over 15 sec. on the test panel where the needle was positioned. The solutions were allowed to sit undisturbed to equilibrate and spread for 3-4 min. Deionized $H_2O$ is used as the reference blank. The solutions which spread significantly did not have symmetrical areas. Their dimensions (L×W) were then measured with a ruler.

Photographs of the water droplets spreading pattern on the panels were taken using a Sony DSC-HX10V digital camera. The photos were taken at an angle inside a MM-1 GTI MiniMatcher light booth (GTI Graphic Technology) in order to overcome the challenge of being able to see the clear transparent liquid patterns on top of the black glossy panel surface. Their dimensions (L×W) were measured with a ruler and are reported.

Coating Evaluation Test Methods for Examples 24-26
ASTM D523: Gloss Measurement was followed using BYK Micro Trigloss meter
ASTM D562: Stormer Viscosity
ASTM D714: Blister Resistance
ASTM D6736 Early Block Resistance
ASTM D1849: Storage Stability
ASTM D2486: Scrub Resistance
ASTM D4062: Leveling
ASTM D4287: Cone & Plate ICI
ASTM D4400: Sag Resistance
ASTM D4828: Washability
ASTM D 6736: Burnish Resistance
ASTM D7190: Surfactant leaching
ASTM D8020: Freeze Thaw stability
Modifications that were Made to the ASTM Methods D4287 Cone & Plate ICI testing was followed except that the hold time was 5 seconds instead of 30 seconds.
D523 Gloss Measurement was followed using BYK Micro Trigloss meter.
D6736 Burnish Resistance was followed except that the cheesecloth was wrapped around a dry sponge which was inserted into the sponge holder before the machine was turned on.
D8020 Freeze Thaw stability—Wetting agents were added at 0.60% on total paint weight to differentiate their advantage on freeze thaw stability. Samples were mixed on Red Devil shaker and tested for paint uniformity and smoothness. Paints that were uniform and smooth were rated pass. Paints that gelled and could not be mixed after shaking to uniform consistency were rated as fail.

Test A1: Roller Foaming

Foaming tendency of a wetting agent was tested by roller application. This was achieved by pouring approximately 5 to 10 grams of test samples side by side directly onto a Leneta Sag and Flow chart (Form 7B) and then making one downward pass with the roller through the slurry using a 9" wide ⅜" nap Purdy roller. The amount of foam generated was visually assessed and qualitatively ranked against the control (without wetting agent) using the following rating: 10—Excellent; 7—Good; 4—Fair; 1—Poor.

Test A2: Brush Foaming

Foaming tendency of wetting agent was carried out by taking a 2" flat Gen X Chinex brush that was dipped into a container with the test sample and applying three brush strokes to a Leneta Sag and Flow chart (Form 7B). The resulting foam in the film was visually assessed and qualitatively ranked against control (without wetting agent) using the following rating: 10—Excellent; 7—Good; 4—Fair; 1—Poor.

Test B: Roller Stability 250 grams of the test sample was placed in a ½ pint container and subjected to mechanical agitation (roller) by using an agitator @ 153 rpm for a period of 24 hours and 12 days.

Test Method C: Color Acceptance

Color acceptance was measures using 8 oz of colorant/gallon of paint. The colorant was Colortrend Lamp Black 808B. The test paint is described in Example 26.

Test Method D: Blush/Color change upon water contact

Test panels were cured for 24 hours at 25° C. They were then subjected to water contact for 2 hours and visually assessed for color change.

Test Method E: Tint Strength Test Method

Purpose: to determine relative tint strength of a white pastel base paint.

The formulation of the base paint is described in Example 26. Tint strength was measures using 2 oz of colorant/gallon of paint. The colorant was Colortrend Lamp Black 808B. Tint strength was measured using a Datacolor Colorimeter.

Procedure for Tint strength
1. Prepare a tinted paint as per above at 2 oz colorant per Gallon of paint.
2. Place on Red devil shaker for 5 minutes.
3. Allow to rest in a controlled temperature cabinet or water bath at 25° C. for 30 minutes 4. Prepare a side by side drawdown with the control paint which has been tinted in the same way using a 3 mil Bird bar on a Penopac chart (e.g., Leneta Form 1B)
5. Allow to dry in a controlled temperature and humidity environment (25±5° C.; 50±5% humidity).
6. Measure tint strength of the test sample and compare to control paint.

Test Method F: Substrate Wettability

The wetting ability of wetting agent was carried out by taking a 2" flat Gen X Chinex brush that was dipped into a container with the test sample and applying minimum amount of test sample with brush held perpendicular to the substrate and dragging it to generate brush marks. Allow 5 mins. for the sample to flow and then assess the substrate for film defects. The resulting wetting defects manifested as crawling in the film was visually assessed and qualitatively ranked against control (without wetting agent) using the following rating: 10—Excellent; 7—Good; 4—Fair; 1—Poor.

EXAMPLES

The following examples further describe and demonstrate illustrative embodiments within the scope of the present invention. The examples are given solely for illustration and are not to be construed as limitations of this invention as many variations are possible without departing from the spirit and scope thereof.

Example 1

In a clean and dry, four liter, steel pressure reactor, equipped with a mechanical stirrer, a nitrogen inlet, a vacuum outlet, an ethylene oxide/propylene oxide inlet, a thermometer and a pressure sensor, 2-ethylhexanol (1020.9 g) was charged. A solution of 50 wt % KOH in water (8.8 g) was added and the mixture was heated to 120° C., while sparging with nitrogen. Water was removed during 2.5 hours under these conditions, the final water concentration was 0.06 wt %, with a total distillate weight of 16.3 g. Propylene oxide (887 g) was added at 120° C. during±1.5 hours. After addition was complete the reaction mixture was held at 120° C. until the pressure was stable (±2 hours). The mixture was heated to 140° C. and ethylene oxide (1346 g) was added during ±2 hours. After addition was complete the reaction mixture was held at 140° C. until the pressure was stable (±0.5 hours). The reaction mixture was cooled to 50° C. and removed from the reactor, yielding 3217 g of a clear, colorless liquid. OH value: 131.26 mg KOH/g; Acid value: 0.06 mg KOH/g; pH (1% in water): 6.6.

Example 2

A four-necked, 500 mL round bottom flask was fitted with a mechanical stirrer, a thermometer, a stopper and a reflux condenser topped with a gas inlet tube. The round bottom flask was charged with Example 1 (100 g) and para-toluenesulfonic acid monohydrate (1.8 g). Methylal (200 g) was charged in one addition. The mixture was refluxed at ±50° C. for 12 hours. Sodium carbonate (0.5 g) in water (5 mL) was added and the resulting mixture was stirred for 30 minutes. The mixture was filtered through celite, after which all volatiles were removed at reduced pressure (30 mbar, 50° C.), yielding 107.34 g of a cloudy, colorless liquid. OH value: 32.8 mg KOH/g; Acid value: 1.1 mg KOH/g; pH (1% in water): 4.6.

Example 3

In a 500 ml, four-necked round bottom flask, filled with a nitrogen atmosphere and equipped with a mechanical stirrer, a thermometer, a reflux condenser and a gas inlet tube, para-toluenesulfonic acid monohydrate (1.88 g) was dissolved in Example 1 (100 g). The mixture was stirred at room temperature and dimethoxymethane (200.00 g) was added in multiple aliquots. Between additions of dimethoxymethane aliquots, the mixture was alternatively heated to reflux followed by vacuum distillation, at ±30 mbar and 55-60° C., to remove volatiles. The mixture was reacted for 12 hours. Sodium carbonate (1.05 g) was dissolved in the minimum amount of water (±5 mL) and added to the reaction mixture. White solid precipitated out of solution. All volatiles were removed under reduced pressure. The resulting mixture was filtered, yielding 107.34 g of a cloudy, colorless liquid. OH value: 32.8 mg KOH/g; Acid value: 1.1 mg KOH/g; pH (1% in water): 4.6.

Example 4

In a clean and dry, 1 liter, glass pressure reactor, equipped with a mechanical stirrer, a nitrogen inlet, a butylene oxide inlet, a thermometer and a pressure sensor, 4-methyl-2-pentanol (771.8 g) was charged. Sodium methanolate (2.32 g) was added and the mixture was heated to 100-125° C. The reactor was opened to the atmosphere and, while sparging with nitrogen, methanol was deionized off during ±2 hours. The reactor was closed, the mixture heated to 130-140° C. and butylene oxide (423 g) was added over 12 hours. The mixture was cooled to room temperature and discharged from the reactor yielding 506.8 g of a brown liquid. OH value: 171.8 mg KOH/g; Acid value: 3.2 mg KOH/g; pH (1% in water): 10.3. The brown liquid (359.8 g) was transferred to a clean and dry, four liter, steel pressure reactor, equipped with a mechanical stirrer, a nitrogen inlet, a vacuum outlet, an ethylene oxide/propylene oxide inlet, a thermometer and a pressure sensor. The mixture was sparged with nitrogen and heated to 140° C. for 30 minutes. Ethylene oxide (194 g) was added at 140° C. during about 0.5 hours. After addition was complete the reaction mixture was held at 140° C. until the pressure was stable (±0.5 hours). The reaction mixture was cooled to 50° C. and neutralized with 0.63 g acetic acid. 192 g of a brown liquid was removed from the reactor: OH value: 110 mg KOH/g; Acid value: 0.2 mg KOH/g; pH (1% in water): 5.9.

Example 5A

In a clean and dry, four liter, steel pressure reactor, equipped with a mechanical stirrer, a nitrogen inlet, a vacuum outlet, an ethylene oxide/propylene oxide inlet, a thermometer and a pressure sensor, 2-ethylhexanol (771.8 g) was charged. A solution of 50 wt % KOH in water (8.9 g) was added and the mixture was heated to 120° C., while sparging with nitrogen. Water was removed during 2.5 hours under these conditions, the final water concentration was 0.08 wt %, with a total distillate weight of 21.8 g. Propylene oxide (662 g) was added at 120° C. during ±1.5 hours. After addition was complete the reaction mixture was held at 120° C. until the pressure was stable (±2 hours). The mixture was heated to 140° C. and ethylene oxide (1506 g) was added during ±2 hours. After addition was complete the reaction mixture was held at 140° C. until the pressure was stable (±0.5 hours). The reaction mixture was cooled to 40° C. and 944.1 g of a clear colorless liquid was removed from the reactor, which was neutralized with 3.68 g acetic acid: OH value: 112.9 mg KOH/g; Acid value: 0.13 mg KOH/g, pH (1% in water): 6.0.

Example 5B

The product mixture remaining in the reactor, from Example 5A, was heated to 140° C. and 339 g of ethylene oxide was added over ±0.25 hours. After addition was complete the reaction mixture was held at 140° C. until the pressure was stable (±0.5 hours). The reaction mixture was cooled to 40° C. and 907 g of a clear colorless liquid was removed from the reactor, which was neutralized with 3.05 g acetic acid: OH value: 96.4 mg KOH/g; Acid value: 0.12 mg KOH/g, pH (1% in water): 6.1.

Example 5C

The product mixture remaining in the reactor, from Example 5A, was heated to 140° C. and 205 g of ethylene oxide was added over ±0.25 hours. After addition was complete the reaction mixture was held at 140° C. until the pressure was stable (±0.5 hours). The reaction mixture was cooled to 70° C. and 1580 g of a clear colorless liquid was removed from the reactor, which was neutralized with 4.78 g acetic acid: OH value: 83.6 mg KOH/g; Acid value: 0.14 mg KOH/g, pH (1% in water): 6.1. The mixture was then cooled to 40° C. and 964.7 g of a clear colorless liquid was removed from the reactor Example 6

A four-necked, 500 mL round bottom flask was fitted with a mechanical stirrer, a thermometer, a stopper and a soxhlet set-up, topped with a gas inlet tube and containing 4 Å molecular sieve. The round bottom flask was charged with Example 5C (100 g), lithium bromide (0.51 g) and para-toluenesulfonic acid monohydrate (1.13 g). Methylal (200 g) was charged in one addition. The mixture was refluxed at ±50° C. for 12 hours. Triethyl amine (0.716 g) was added and the resulting mixture was stirred for 30 minutes. The mixture was filtered through celite, after which all volatiles were removed at reduced pressure (30 mbar, 50° C.), yielding 106.05 g of a clear, yellow liquid. OH value: 5.4 mg KOH/g; Acid value: 0.58 mg KOH/g; pH (1% in water): 4.8. A 0.3 wt. % solution of Example 6 in deionized water exhibited a static surface tension of 29.71 mN/m. A 0.3 wt. % solution of Example 6 in deionized water exhibited a dynamic surface tension of 45 mN/ms at 10 ms.

Example 7

In a clean and dry, four liter, steel pressure reactor, equipped with a mechanical stirrer, a nitrogen inlet, a vacuum outlet, an ethylene oxide/propylene oxide inlet, a thermometer and a pressure sensor, 3,5,5-trimethylhexanol (809.4 g) was charged. A solution of 50 wt % KOH in water (6.5 g) was added and the mixture was heated to 120° C., while sparging with nitrogen. A vacuum of 0.3 bar was applied and after was deionized off during 1 hour, the final water concentration was 0.01 wt %. Propylene oxide (647 g) was added at 120° C. during ±2 hours. After addition was complete the reaction mixture was held at 120° C. until the pressure was stable (±2 hours). The mixture was heated to 140° C. and ethylene oxide (986 g) was added during ±2 hours. After addition was complete the reaction mixture was held at 140° C. until the pressure was stable (±0.5 hours). The reaction mixture was cooled to 60° C. and removed from the reactor, yielding 2413 g of a clear, colorless liquid. OH value: 127.5 mg KOH/g; Base value: 1.04 mg KOH/g.

Example 8

In a 500 ml, four-necked round bottom flask, filled with a nitrogen atmosphere and equipped with a mechanical stirrer, a thermometer, a reflux condenser and a gas inlet tube, para-toluenesulfonic acid monohydrate (1.88 g) and lithium bromide (0.86 g) were dissolved in Example 7 (100 g). The mixture was stirred at room temperature and dimethoxymethane (75.0 g) was added in multiple aliquots. Between additions of dimethoxymethane aliquots, the mixture was alternatively heated to reflux followed by vacuum distillation, at ±30 mbar and 55-60° C., to remove volatiles. The mixture was reacted for 3 hours. Sodium carbonate (1.05 g) was dissolved in the minimum amount of water (±5 mL) and added to the reaction mixture. White solid precipitated out of solution. All volatiles were removed under reduced pressure. The resulting mixture was filtered, yielding 104 g of a clear, slightly yellow mixture, to which 1 g of water was added. OH number: 19.6 mg KOH/g; Acid number: 0.1 mg KOH/g; pH (1% in water): 7.9. A 0.3 wt. % solution of Example 8 in deionized water exhibited a static surface tension of 28.51 mN/m. A 0.3 wt. % solution of Example 8 in deionized water exhibited a dynamic surface tension of 35 mN/ms at 10 ms.

Example 9

In a clean and dry, four liter, steel pressure reactor, equipped with a mechanical stirrer, a nitrogen inlet, a vacuum outlet, an ethylene oxide/propylene oxide inlet, a thermometer and a pressure sensor, octanol (699.6 g) was charged. A solution of 50 wt % KOH in water (5.01 g) was added and the mixture was heated to 135° C., while sparging with nitrogen. A vacuum of 0.3 bar was applied and water was removed during 2 hour, the final water concentration was 0.08 wt %. Propylene oxide (616 g) was added at 120° C. during ±1.5 hours. After addition was complete the reaction mixture was held at 120° C. until the pressure was stable (±2 hours). The mixture was heated to 140° C. and ethylene oxide (934 g) was added during ±2 hours. After addition was complete the reaction mixture was held at 140° C. until the pressure was stable (±0.5 hours). The reaction mixture was cooled to 50° C. and removed from the reactor, yielding 2227.4 g of a clear, colorless liquid. OH value: 137.8 mg KOH/g; Acid value: 0.13 mg KOH/g; pH (1% in water): 6.3.

Example 10

A four-necked, 500 mL round bottom flask was fitted with a mechanical stirrer, a thermometer, a stopper and a soxhlet set-up, topped with an Example 9 (100 g), lithium bromide (0.825 g) and para-toluenesulfonic acid monohydrate (1.8 g). Methylal (200 g) was charged in one addition. The mixture was refluxed at ±50° C. for 12 hours. Potassium carbonate (0.1.32 g) was added and the resulting mixture was stirred for 30 minutes. The mixture was filtered through celite, after which all volatiles were removed at reduced pressure (30 mbar, 50° C.), yielding 105.74 g of a clear yellow liquid. OH value: 25.4 mg KOH/g; Acid value: 0.5 mg KOH/g; pH (1% in water): 4.5.

Example 11

In a clean and dry, four liter, steel pressure reactor, equipped with a mechanical stirrer, a nitrogen inlet, a vacuum outlet, an ethylene oxide/propylene oxide inlet, a thermometer and a pressure sensor, isononanol (1000 g) was charged. A solution of 50 wt % KOH in water (7.9 g) was added and the mixture was heated to 120° C., while sparging with nitrogen. A vacuum of 0.3 bar was applied and water was removed during 2 hour, the final water concentration was 0.06 wt %. Propylene oxide (798 g) was added at 120° C. during ±1.5 hours. After addition was complete the reaction mixture was held at 120° C. until the pressure was stable (±2 hours). The mixture was heated to 140° C. and ethylene oxide (1211 g) was added during ±2 hours. After addition was complete the reaction mixture was held at 140° C. until the pressure was stable (±0.5 hours). The reaction mixture was cooled to 50° C. and neutralized with acetic acid (5.3 g), yielding 2931.8 g of a clear, colorless liquid. OH value: 127.1 mg KOH/g; Acid value: 0.09 mg KOH/g.

Example 12

A four-necked, 500 mL round bottom flask was fitted with a mechanical stirrer, a thermometer, a stopper and a reflux condenser topped with a gas inlet tube. The round bottom flask was charged with Example 11 (100 g), lithium bromide (0.825) and para-toluenesulfonic acid monohydrate (1.8 g). Methylal (200 g) was charged in one addition. The mixture was refluxed at ±50° C. for 12 hours. Sodium carbonate (1.0 g) was added and the resulting mixture was stirred for 30 minutes. The mixture was filtered through celite, after which all volatiles were removed at reduced pressure (30 mbar, 50° C.), yielding 107.13 g of a clear yellow liquid. OH value: 12.3 mg KOH/g; Acid value: 1 mg KOH/g; pH (1% in water): 4.1.

Example 13

In a clean and dry, four liter, steel pressure reactor, equipped with a mechanical stirrer, a nitrogen inlet, a vacuum outlet, an ethylene oxide/propylene oxide inlet, a thermometer and a pressure sensor, isononanol (760.6 g) was charged. A solution of 50 wt % KOH in water (13.9 g) was added and the mixture was heated to 130° C., while sparging with nitrogen. A vacuum of 0.3 bar was applied and water was removed during 2 hour, the final water concentration was 0.02 wt %. The mixture was heated to 160° C. and ethylene oxide (1158.5 g) was added during ±2 hours. After addition was complete the reaction mixture was held at 160° C. until the pressure was stable (±0.5 hours). The mixture was cooled to 135° C. and propylene oxide (916.5 g) was then added at during ±1.5 hours. After addition was complete, the reaction mixture was heated to 170-180° C. until the pressure was stable (±0.25 hours). The mixture was then cooled to 40° C. and 1004 g of a clear colorless liquid was removed from the reactor, which was neutralized with 1.21 g acetic acid: OH value: 98.17 mg KOH/g; Acid value: 1.7 mg KOH/g.

Example 14

A four-necked, 500 mL round bottom flask was fitted with a mechanical stirrer, a thermometer, a stopper and a reflux condenser topped with a gas inlet tube. The round bottom flask was charged with Example 13 (100 g), lithium bromide (0.6) and para-toluenesulfonic acid monohydrate (1.33 g). Methylal (200 g) was charged in one addition. The mixture was refluxed at ±50° C. for 12 hours. Sodium carbonate (0.95 g) was added and the resulting mixture was stirred for 30 minutes. The mixture was filtered through celite, after which all volatiles were removed at reduced pressure (30 mbar, 50° C.), yielding 106.52 g of a cloudy, colorless liquid. OH value: 17.7 mg KOH/g; Acid value: 2.4 mg KOH/g; pH (1% in water): 4.3.

Example 15

In a clean and dry, four liter, steel pressure reactor, equipped with a mechanical stirrer, a nitrogen inlet, a vacuum outlet, an ethylene oxide/propylene oxide inlet, a thermometer and a pressure sensor, isononanol (760.6 g) was charged. A solution of 50 wt % KOH in water (13.9 g) was added and the mixture was heated to 130° C., while sparging with nitrogen. A vacuum of 0.3 bar was applied and water was removed during 2 hour, the final water concentration was 0.02 wt %. The mixture was heated to 160° C. and ethylene oxide (1158.5 g) was added during ±2 hours. After addition was complete the reaction mixture was held at 160° C. until the pressure was stable (±0.5 hours). The mixture was cooled to 135° C. and propylene oxide (916.5 g) was then added at during ±1.5 hours. After addition was complete, the reaction mixture was heated to 170-180° C. until the pressure was stable (±0.25 hours). The mixture was then cooled to 40° C. and 1004 g of a clear colorless liquid was removed from the reactor. The product mixture remaining in the reactor was heated to 140° C. and 197.3 g of propylene oxide was added over ±0.25 hours. After addition was complete, the reaction mixture was heated to 170-180° C. until the pressure was stable (±0.25 hours). The mixture was then cooled to 40° C. and 964.7 g of a clear colorless liquid was removed from the reactor, which was neutralized with 1.05 g acetic acid: OH value: 89.7 mg KOH/g; Acid value: 1.5 mg KOH/g.

Example 16

A four-necked, 500 mL round bottom flask was fitted with a mechanical stirrer, a thermometer, a stopper and a reflux condenser topped with a gas inlet tube. The round bottom flask was charged with Example 15 (100 g), lithium bromide (0.55 g) and para-toluenesulfonic acid monohydrate (1.22 g). Methylal (200 g) was charged in one addition. The mixture was refluxed at ±50° C. for 12 hours. Sodium carbonate (1.02 g) was added and the resulting mixture was stirred for 30 minutes. The mixture was filtered through celite, after which all volatiles were removed at reduced pressure (30 mbar, 50° C.), yielding 102.73 g of a clear yellow liquid. OH value: 25.8 mg KOH/g; Acid value: 2.0 mg KOH/g; pH (1% in water): 4.4.

Example 17

In a clean and dry, four liter, steel pressure reactor, equipped with a mechanical stirrer, a nitrogen inlet, a vacuum outlet, an ethylene oxide/propylene oxide inlet, a thermometer and a pressure sensor, isononanol (405.6 g) was charged. A solution of 50 wt % KOH in water (3.9 g) was added and the mixture was heated to 120° C., while sparging with nitrogen. A vacuum of 0.3 bar was applied and water was removed during 1 hour, the final water concentration was 0.04 wt. %. Propylene oxide (484 g) was added at 120° C. during ±1.5 hours. After addition was complete the reaction mixture was held at 120° C. until the pressure was stable (±2 hours). The mixture was heated to 140° C. and ethylene oxide (612 g) was added during ±2 hours. After addition was complete the reaction mixture was held at 140° C. until the pressure was stable (±0.5 hours). The reaction mixture was cooled to 50° C. and neutralized with 5.03 g 2-ethylhexanoic acid. The product was removed from the reactor, yielding 1482.9 g of a clear, colorless liquid. OH value: 109.5 mg KOH/g; Acid value: 0.12 mg KOH/g.

Example 18

In a 500 ml, four-necked round bottom flask, filled with a nitrogen atmosphere and equipped with a mechanical stirrer, a thermometer, a reflux condenser and a gas inlet tube, para-toluenesulfonic acid monohydrate (1.48 g) and lithium bromide (0.68 g) were dissolved in Example 17 (100 g). The mixture was stirred at room temperature and dimethoxymethane (59.4 g) was added in multiple aliquots. Between additions of dimethoxymethane aliquots, the mixture was alternatively heated to reflux followed by vacuum distillation, at ±30 mbar and 55-60° C., to remove volatiles. The mixture was reacted for 3 hours. Sodium carbonate (0.83 g) was dissolved in the minimum amount of water (±5 mL) and added to the reaction mixture. White solid precipitated out of solution. All volatiles were removed under reduced pressure. The resulting mixture was filtered, yielding 97.78 g of a clear, colorless mixture, to which 1 g of water was added. OH number: 27.3 mg KOH/g; Acid number: 0.6 mg KOH/g; pH (1% in water): 5.3.

Example 19

In a 500 ml, four-necked round bottom flask, filled with a nitrogen atmosphere and equipped with a mechanical stirrer, a thermometer, a reflux condenser and a gas inlet tube, para-toluenesulfonic acid monohydrate (1.5 g) and lithium bromide (0.68 g) were dissolved in Example 4 (100 g). The mixture was stirred at room temperature and dimethoxymethane (59.8 g) was added in multiple aliquots. Between additions of dimethoxymethane aliquots, the mixture was alternatively heated to reflux followed by vacuum distillation, at ±30 mbar and 55-60° C., to remove volatiles. The mixture was reacted for 3 hours. Sodium carbonate (0.83 g) was dissolved in the minimum amount of water (±5 mL) and added to the reaction mixture. White solid precipitated out of solution. All volatiles were removed under reduced pressure. The resulting mixture was filtered, yielding 89.29 g of a yellow, turbid mixture, to which 0.9 g of water was added. OH number: 32.8 mg KOH/g; Acid number: 0.2 mg KOH/g; pH (1% in water): 5.8. A 0.3 wt. % solution of Example 19 in deionized water exhibited a static surface tension of 29.08 mN/m. A 0.3 wt. % solution of Example 19 in deionized water exhibited a dynamic surface tension of 40 mN/ms at 10 ms.

Example 20

In a clean and dry, four liter, steel pressure reactor, equipped with a mechanical stirrer, a nitrogen inlet, a vacuum outlet, an ethylene oxide/propylene oxide inlet, a thermometer and a pressure sensor, isononanol (759 g) was charged. A solution of 50 wt % KOH in water (6.4 g) was added and the mixture was heated to 130° C., while sparging with nitrogen. A vacuum of 0.3 bar was applied and water was removed during 2 hour, the final water concentration was 0.09 wt. %. The mixture was heated to 140° C. and ethylene oxide (464 g) was added during ±2 hours. After addition was complete the reaction mixture was held at 140° C. until the pressure was stable (±0.5 hours). The mixture was cooled to 120° C. and propylene oxide (611.5 g) was added during ±1.5 hours. After addition was complete the reaction mixture was held at 120° C. until the pressure was stable (±4 hours). The mixture was heated to 140° C. and ethylene oxide (696 g) was added during ±2 hours. After addition was complete the reaction mixture was held at 140° C. until the pressure was stable (±0.5 hours). The reaction mixture was cooled to 50° C. and the product was removed from the reactor, yielding 2496 g of a clear, colorless liquid. OH value: 117.5 mg KOH/g; Base value: 0.02 meq/g; pH (1% in water): 9.8.

Example 21

In a 500 ml, four-necked round bottom flask, filled with a nitrogen atmosphere and equipped with a mechanical stirrer, a thermometer, a reflux condenser and a gas inlet tube, para-toluenesulfonic acid monohydrate (2.37 g) and lithium bromide (1.08 g) were dissolved in Example 20 (150 g). The mixture was stirred at room temperature and dimethoxymethane (94.93 g) was added in multiple aliquots. Between additions of dimethoxymethane aliquots, the mixture was alternatively heated to reflux followed by vacuum distillation, at ±30 mbar and 55-60° C., to remove volatiles. The mixture was reacted for 3 hours. Sodium carbonate (1.32 g) was dissolved in the minimum amount of water (±4 mL) and added to the reaction mixture. White solid precipitated out of solution. All volatiles were removed under reduced pressure. The resulting mixture was filtered, yielding 145.9 g of a colorless, clear mixture, to which 1.5 g of water was added. OH number: 36.9 mg KOH/g; Acid number: 0.1 mg KOH/g; pH (1% in water): 9.6.

Example 22

Test Procedure for Testing Foaming of Wetting Agents in Deionized Water

Low foam wetting agents described in the previous examples were measured according to the foam testing procedure described herein. Foam test was also carried out on a number of commercial wetting agents. These include: (1) an acetylenic diol gemini surfactant composition (Surfynol™ 104H), (2) an alkyl ethoxylate surfactant composition (Multiwet™ SU) and (3) an alkyl phenol ethoxylate (Triton™ CF10).

The results are summarized in Table 1.

TABLE 1

Foam Test Data

| Example No. | Foam Height Immediate after blowing air, cm ± 0.2 cm | Foam Height 5 mins, wait time after blowing air, cm ± 0.2 cm |
|---|---|---|
| 1 | 0.42 | 0.00 |
| 3 | 0.00 | 0.00 |
| 5 | 12.75 | 0.00 |
| 6 | 1.36 | 0.00 |
| 7 | 1.27 | 0.42 |
| 8 | 0.00 | 0.00 |
| 9 | 17.00 | 1.70 |
| 10 | 0.00 | 0.00 |
| 12 | 0.00 | 0.00 |
| 15 | 4.76 | 0.85 |
| 14 | 0.00 | 0.00 |
| 15 | 0.00 | 0.00 |
| 16 | 0.00 | 0.00 |
| 17 | 19.00 | 1.70 |
| 18 | 0.00 | 0.00 |
| 4 | 18.20 | 1.70 |
| 19 | 4.00 | 0.30 |

TABLE 1-continued

Foam Test Data

| Example No. | Foam Height Immediate after blowing air, cm ± 0.2 cm | Foam Height 5 mins, wait time after blowing air, cm ± 0.2 cm |
|---|---|---|
| 20 | 18.20 | 0.90 |
| 21 | 0.00 | 0.00 |
| Gemini Diol | 0.00 | 0.00 |
| Alkyl Ethoxylate | 17.00 | 3.40 |
| Alkyl Phenol Ethoxylate | 17.00 | 0.85 |

Example 23

DST measurements were evaluated for an inventive example and three commercial examples: (1) Example 8, (2) an acetylenic diol gemini surfactant composition (Surfynol™ 104H), (3) an alkyl ethoxylate surfactant composition (Multiwet™ SU) and (4) an alkyl phenol ethoxylate (Triton™ CF10). The testing was done using a Kruss™ BP2 Bubble Tensiometer. As much as was possible, solution concentrations were kept the same or very close. Three of the wetting agents had concentrations of 0.25%-0.30% in deionized water. The gemini diol had limited solubility in water and could only be added at a concentration of 0.1%. Surface ages were increased from 10 ms up to about 50,000 ms. A reference material to be used for comparison is deionized water which has a DST result of 72-73 mN/m.

The results from the DST testing are shown in the FIGURE. Surface age in milliseconds (ms) is shown on the X-axis, and the solution surface tension is shown on the Y-axis. The alkyl phenol ethoxylate and the gemini diol wetting agents do not provide the same level of surface tension reduction compared to the other two. Their surface tension reduction does improve with increasing surface age and eventually levels out at about 34 mN/m at surface ages greater than 5000 ms. The wetting agent of Example 8 provides better surface tension reduction than the gemini diol and alkyl phenol ethoxylate at all measured surface ages, and it is competitive with the alkyl ethoxylate at surface ages greater than 500 ms.

SST measurements were performed on the four wetting agents described above. All four wetting agents were evaluated at the 0.3% concentration in deionized water. The measured SST values of the four wetting agents are as follows:

| Example 8 | 27.2 mN/m |
| Alkyl phenol ethoxylate | 33.6 mN/m |
| Alkyl ethoxylate | 26.3 mN/m |
| Gemini diol | 32.1 mN/m |

Example 8 has a lower SST than the alkyl phenol ethoxylate and the gemini diol, and is close to the SST of alkyl ethoxylate. The alkyl ethoxylate has an SST which is 1.1 mN/m lower than the result for Example 8, however, the wetting agent alkyl ethoxylate suffers from the adverse defect of producing much foam during its use in coating preparations and applications. deionized Example 24

Wetting Performance on Wood Lacquer

Varnish coated wood surfaces may sometimes be low surface energy and difficult to wet-out. For this reason wetting agents are added to water based wood coating lacquers to improve substrate wetting. Wood lacquers are typically applied by brush, spray, and sometimes by roller. These application processes can incorporate foam into the lacquer coating. Foam trapped in dried film adversely impacts the film's protective property as well as its appearance. Table 2 shows the clear wood lacquer formula which was used to evaluate the performance of four types of wetting agents.

TABLE 2

Clear wood lacquer formula.

| Raw Material | Pounds | Function | Supplier |
|---|---|---|---|
| Resin: Essential R6010 | 88.45 | Binder | Essential Polymers |
| Water | 4.65 | Solvent | — |
| Dowanol™ DPM | 3.14 | Coalescent | DOW Chemical |
| Dowanol™ DPnB | 3.14 | Coalescent | DOW Chemical |
| Test Sample | 0.30 | Wetting Agent | various |
| Rheolate® 658 | 0.32 | Associative Thickener | Elementis Specialties |
| Total | 100.00 | — | — |

Application foam tests were carried out for the four wetting agents described in example 24, as well as a control without wetting agent, as per Test methods A1 and A2. The amount of foam generated during application by each of the different application methods were ranked relative to the control.

Table 3 shows results for the different modes of application for the control and four wetting agent modified lacquers. Each of the lacquers had comparable viscosity and gloss. The major differences between the wetting agents stand out in the foam generated during the different methods of application. Based on the results for brush and roller applications, the gemini diol and the Example 8 wetting agent appear to cause fewer problems associated with foaming. The two remaining wetting agents could be problematic during roller application.

TABLE 3

Paint and dry film test properties of the different wetting agents in the clear wood lacquer formula.

| Wetting Agent | Control (none) 3401-22 | Example #8 3401-23-B | Alkyl Phenol Ethoxylate 3401-23-C | Alkyl Ethoxylate 3401-23-D | Gemini Diol 3401-23-E |
|---|---|---|---|---|---|
| Brookfield Viscosity (50 rpm, cps) | 107 | 107 | 107 | 102 | 110 |
| Gloss by Drawdown 20° | 76 | 76 | 75 | 77 | 77 |
| 60° | 90 | 90 | 91 | 91 | 91 |
| Gloss by Spray 20° | 72 | 75 | 75 | 75 | 74 |
| 60° | 90 | 91 | 91 | 90 | 91 |
| Wettability Test F | 3 | 8 | 7 | 9 | 4 |
| Foaming by Brushing | 8 | 7 | 6 | 3 | 8 |

TABLE 3-continued

Paint and dry film test properties of the different wetting agents in the clear wood lacquer formula.

| Wetting Agent | Control (none) 3401-22 | Example #8 3401-23-B | Alkyl Phenol Ethoxylate 3401-23-C | Alkyl Ethoxylate 3401-23-D | Gemini Diol 3401-23-E |
|---|---|---|---|---|---|
| Foaming by Roller | 7 | 6 | 5 | 1 | 6 |
| Foaming by Spray | 9 | 9 | 9 | 9 | 9 |

Rating: 10-Excellent; 7-Good; 4-Fair; 1-Poor.

Example 25

Pigment Wetting

Wetting of pigments is essential to get optimum pigment dispersion. Pigment particles present as agglomerates are surrounded with air that must be displaced by liquid for wetting of the particles to take place. The wetting step involves replacing adsorbed materials on the pigment surface with liquid. If the surface tension of the liquid is higher than the surface energy of the pigment then it will not wet the pigment surface.

Water alone is unable to wet the surface of many pigments due to its higher surface tension than the surface energy of the pigments. Wetting agents are added to lower the surface tension of water and aid pigment wetting by adsorbing and orienting on the liquid-air interface resulting in lowering the interfacial tension.

Wetting agents apart from reducing the surface tension of water also have a tendency of stabilizing foam. Foam generated during production can interfere with the dispersion process affecting opacity and color development, increase production time and compromising product quality.

The ability of the inventive wetting agents to provide adequate wetting of pigments without excessive foam production was demonstrated in the grind stage of a typical waterborne coating. The grind stage involves the wetting and dispersion of $TiO_2$, resulting in a $TiO_2$ slurry. The performance of the inventive wetting agent was compared to the commercial wetting agents listed in Table 3.

Table 4 shows the formulation used to make a $TiO_2$ slurry. Wetting agents were added at 0.97% actives on $TiO_2$ weight. Defoamer was intentionally left out to capture the foaming tendency differences of the wetting agents.

TABLE 4

Titanium Dioxide Slurry Formula

| Raw Material | Pounds | Function | Supplier |
|---|---|---|---|
| Water | 26.00 | Solvent | — |
| Proxel ™ GXL | 0.20 | Biocide | Arch Chemicals |
| Nuosperse ® FX665 | 1.50 | Dispersant | Elementis Specialties |
| Non Ionic Surfactant | 0.70 | Wetting Agent | Various suppliers |
| $TiO_2$ DuPont R706 | 71.60 | Pigment | Du Pont |
| | Mix using a Dispermat ™ @ 500 rpm for 10 mins; tip speed = 1.31 m/s Check grind | | |
| Total | 100.00 | | |

The foaming tendency of each wetting agent used in the $TiO_2$ slurry was tested by roller application, according to Test A1.

Table 5 shows the evaluation results of $TiO_2$ slurries based on four wetting agents. Each of the slurries had comparable grind, viscosity and gloss. The major differences between the wetting agents stand out in the foam generated during the making of $TiO_2$ slurry. The gemini diol and the Example 8 wetting agent resulted in significantly less foam than the alkyl phenol ethoxylate and alkyl ethoxylate based slurry.

The Gemini diol based $TiO_2$ slurry showed excessive grit upon drawing down on a Leneta Form 1B opacity chart using a 3 mil Bird applicator. Grit appears to be small gel particles which could not be captured on the grind gage. The soft gel particles may be related to the low solubility of gemini diol in water. The low foaming characteristics of gemini diol could possibly be due to its low water solubility.

Excess foam generated during the grind stage may result in prolonged grind time resulting in the loss of production time and an inferior quality of the finished product. Addition of excess defoamer to overcome foam will increase product cost and possibly compromise the final film properties.

TABLE 5

Test results of the different wetting agents in the $TiO_2$ Slurry formula.

| Wetting Agent | | Example 8 | Alkyl Phenol Ethoxylate | Alkyl Ethoxylate | Gemini Diol |
|---|---|---|---|---|---|
| Brookfield Viscosity (50 rpm, cps) | | 354 | 480 | 326 | 312 |
| Gloss by Drawdown | 20° | 70+ | 70+ | 70+ | 70+ |
| | 60° | 90+ | 90+ | 90+ | 90+ |
| Hegman Grind | | 8 | 8 | 7 | 7 |
| Draw Down Appearance | | Smooth | Smooth | Smooth | Gritty |
| Foaming byRoller | | 9 | 1 | 1 | 9 |

Rating: 10-Excellent; 7-Good; 4-Fair; 1-Poor.

Example 26

Application in Decorative Coatings—

Water based coatings are formulated with various ingredients such as solvent, binder, pigments or fillers, surfactants-wetting agents and dispersant, film formers, biocides, defoamers, and rheology modifiers. Wetting agents are used for various purposes in waterborne coatings. These include pigment wetting for optimum dispersion of pigments that provide control of opacity and color development. They promote wetting of low surface energy substrates resulting in improved adhesion to such surfaces. Wetting agents can also be used as leveling aids.

Because water based coatings are marketed as eco-friendly coatings, solvents traditionally used in these coatings have either been removed or significantly reduced in concentration. As a result, the coatings face increased challenges in areas such as freeze thaw stability, shorter open time, and in can paint skinning. Wetting agents are helpful to some extent in such demanding performance properties. However, wetting agents tend to make the coating water sensitive resulting in poor blister and blush resistance, surfactant leaching, foaming, burnishing, film softening and they affect stain resistance. Due to these concerns, the inventive wetting agent was evaluated in a typical waterborne coating and compared to the commercial wetting agents listed in Table 3. Table 6 shows the formulation used to make a test deco coating. Sample wetting agents were added in the let down at 0.30% actives on total paint weight. Ideally the wetting agent should be added before the pigments for wetting the pigments-essential in the dispersion process. However, for this evaluation the wetting agents were added in the letdown to minimize process variability. The formulation had 11.11 pounds/gallon; 53.4 wt. % solids; 37.4 vol. % solids; 27.9% PVC; 0.2 lbs./gal VOC; and 21.0 g/l VOC.

TABLE 6

Formulation of Deco Coating

| Raw Material | Pounds | Function | Supplier |
|---|---|---|---|
| Water | 15.66 | Solvent | — |
| Proxel ™ GXL | 0.10 | Biocide | Arch Chemicals |
| Nuosperse ® FX665 | 1.00 | Dispersant | Elementis Specialties |
| Mix low speed for 2-3mins. | | | |
| Titanium Dioxide R706 | 27.50 | Hide | DuPont |
| Minex ® 7 | 2.50 | Sheen Control | Unimin Corporation |
| Mix @1500 rpm for 5 mins; tip speed 6.28 m/s. Grind 6+ at 1000 rpm; tip speed 4.19 m/s | | | |
| Ammonium Hydroxide | 0.15 | Buffer | Sigma Aldrich |
| Mix 2-3mins. | | | |
| Rhoplex ™ HG706 | 49.34 | Resin | DOW Chemicals |
| Dapro ® DF39 | 0.10 | Defoamer | Elementis Specialties |
| Texanol | 0.60 | Coalescent | Eastman Chemical Company |
| Maintain 1000 rpm; tip speed 4.19 m/s. Add following ingredients | | | |
| Rheolate ® HX6010 | 2.20 | Rheology Modifier | Elementis Specialties |
| Rheolate ® CVS 10 | 0.50 | Rheology Modifier | Elementis Specialties |
| Mix 5 mins. Then add | | | |
| Dapro ® DF39 | 0.35 | Defoamer | Elementis Specialties |
| Total | 100.00 | | |

A master batch, without wetting agent, was made and then split in equal parts. Defoamer was intentionally kept at a minimum in the formula to capture the foaming tendency differences of the wetting agents.

Table 7 shows the evaluation results of the test deco coating based on four wetting agents. Each of the coatings had comparable performance in some application properties. The differences between the wetting agents are seen in their foaming characteristics, color acceptance, tint strength, freeze thaw stability, sag, washability, and early block resistance. Each property was measured by methods described herein.

TABLE 7

Evaluation of deco coating containing different wetting agents.

| | Wetting Agent | None | Example 8 | Alkyl Phenol Ethoxylate | Alkyl Ethoxylate | Gemini Diol |
|---|---|---|---|---|---|---|
| D562 | Viscosity Stormer (KU) | 105 | 101 | 99 | 97 | 104 |
| D4287 (1) | Cone & Plate ICI (Poise) | 1.57 | 1.55 | 1.53 | 1.42 | 1.60 |
| D523 (2) | Gloss (60°/85°) | 39/73 | 39/74 | 38/74 | 43/76 | 40/72 |
| D4400 | Sag mils | 18 | 16 | 12 Drips | 12 Drips | 14 |
| D4062 | Leveling | 9 | 9 | 9 | 9 | 9 |
| | Foaming-Roller | 8 | 7.5 | 6 | 6 | 8 |
| D2486 | Scrub Cycles | 449 | 456 | 462 | 450 | 587 |
| D4828 | Washability | 7 | 6.5 | 6 | 5 | 5.5 |
| D7190 | Surfactant Leaching | Pass | Pass | Pass | Pass | Pass |
| D714 | Blister Resistance (2 hrs. water contact) | 10 | 10 | 10 | 10 | 10 |
| | Blush Resistance (2 hrs. water contact) | 9 | 9 | 9 | 9 | 9 |
| | Tint Strength | 100.00 | 99.12 | 99.37 | 99.05 | 99.91 |
| Test C | Color Acceptance | 9 | 9 | 9 | 9 | 9 |
| D4946 | Early Block Resistance (24 hrs cure; avg. of 3) | 7.7 | 7.3 | 8.3 | 6.0 | 6.7 |
| D6736 (3) | Burnish Resistance (% change in gloss) | Standard | No Change | No Change | No Change | No Change |
| STABILITY DATA | | | | | | |
| Aged @ 60° C. ASTM # D1849 | Viscosity (KU; 12 days) | 93 | 95 | 94 | 91 | 97 |
| | 24 Hrs. Foam | 8 | 7.5 | 6 | 6 | 8 |
| | 12 Days Foam | 8 | 7 | 6 | 6 | 6 |
| Roller Stability Test B | Viscosity (KU; 12 days) | 104 | 102 | 99 | 100 | 106 |
| | 24 Hrs. Foam | 8 | 7 | 5 | 4 | 7 |
| | 12 Days Foam | 8 | 7 | 5 | 4 | 4 |
| Freeze | 1st Cycle | Fail | Pass | Pass | Pass | Fail |

TABLE 7-continued

Evaluation of deco coating containing different wetting agents.

| | Wetting Agent | None | Example 8 | Alkyl Phenol Ethoxylate | Alkyl Ethoxylate | Gemini Diol |
|---|---|---|---|---|---|---|
| Thaw ASTM # D8020 (4) | 2$^{nd}$ Cycle | NA | Pass | Pass | Pass | NA |
| | 3$^{rd}$ Cycle | NA | Pass | Pass | Pass | NA |

Rating: 10-Excellent; 7-Good; 4-Fair; 1-Poor.

Example 27

Water Droplet Spreading Analysis

In order to evaluate the capacity of the inventive wetting agent to impart wetting properties to a water based formulation, a simple experiment was carried out, in which dilute aqueous solutions of wetting agent were prepared and applied to a low energy solid substrate. The degree to which the applied solution spread on the substrate was used as a measure of the performance of the wetting agent. Similar solutions of commercial wetting agents listed in Table 3 were also prepared and added to the substrate in a similar way. A comparison of the spreading rates for these solutions provided a relative measure of the wetting performance for these surfactants, shown in Table 8.

TABLE 8

Test Results

| Liquid | Deposited Liquid Dimensions |
|---|---|
| Blank Test Panel Dimensions | (95 mm × 145 mm) |
| Deionized Water (reference) | 21 mm × 22 mm |
| Example 8 0.3% Aq | 71 mm × 91 mm |
| Alkyl Phenol Ethoxylate 0.3% Aq | 38 mm × 41 mm |
| Alkyl Ethoxylate 0.3% Aq | 76 mm × 105 mm |
| Gemini Diol 0.3% Aq | 31 mm × 37 mm |

From the results listed in Table 8 both the alkyl phenol ethoxylate and gemini diol only provide slight wetting spreading improvement over the blank water sample. The inventive composition and the alkyl ethoxylate both provide much better wetting spreading of the liquid. The ranking results from this spreading experiment are: (1) alkyl ethoxylate; (2) inventive composition; (3) alkyl phenol ethoxylate which is approximately equal to (4) gemini diol. These results are in the same relative order of the measured static surface tension results and the dynamic surface tension results taken from the 30,000-50,000 milliseconds (ms) range of the DST curve.

The present disclosure may be embodied in other specific forms without departing from the spirit or essential attributes of the invention. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A wetting agent comprising 70-99 wt. % of a composition according to Formula (I):

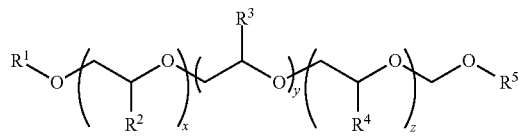

wherein
R$^1$ is selected from a branched alkyl group or linear alkyl group or a cycloaliphatic group or an aromatic group, each having 6 to 15 carbon atoms;
R$^2$ is selected from hydrogen, methyl, or ethyl;
R$^3$ is methyl;
R$^4$ is hydrogen;
R$^5$ is selected from methyl or ethyl;
x is 0;
y ranges from 2 to 5;
z ranges from 3 to 10;
with the proviso that R$^3$ is different from R$^4$ and
1-30 wt. % of a composition according to Formula (II):

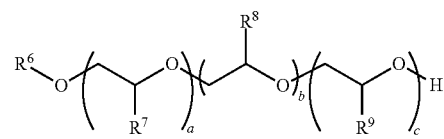

wherein R$^6$ is the same as R$^1$, R$^7$ is the same as R$^2$, R$^8$ is the same as R$^3$ and R$^9$ is the same as R$^4$, a equals x, b equals y and c equals z.

2. The wetting agent according to claim 1, wherein R$^1$ is selected from a branched alkyl group or linear alkyl group or a cycloaliphatic group or an aromatic group, each having 6 to 10 carbon atoms.

3. The wetting agent according to claim 2, wherein R$^1$ is selected from nonyl, isononyl, 3, 5, 5-trimethyl hexyl, octyl, 2-methyl heptyl, 2-ethyl hexyl, 2,2,4-trimethyl pentyl, 4-methyl pentyl, heptyl, and hexyl.

4. The wetting agent according to claim 1, wherein a 0.3 wt. % solution of the wetting agent composition in aqueous solution has a dynamic surface tension ranging from 50 mN/m to 25 mN/m at 1000 ms or less surface age.

5. The wetting agent according to claim 1, wherein a 0.3 wt. % solution of the wetting agent in aqueous solution has a static surface tension ranging from 45 mN/m to 20 mN/m.

6. An aqueous composition comprising an effective amount of the wetting agent according to claim 1, wherein the aqueous composition has a foaming value less than 17 cm when measured at a concentration of 0.3 wt. % immediately after removing an air source according to the foam test procedure and has a foaming value less than 3 cm when measured at a time interval of 5 minutes after removing the air source; wherein the aqueous composition has a static surface tension ranging from 45 mN/m to 25 mN/m, when measured at a concentration of 0.3 wt. %.

7. The aqueous composition according to claim 6, wherein the aqueous composition comprises a latex polymer.

8. The aqueous composition according to claim 6, wherein the aqueous composition comprises a pigment.

\* \* \* \* \*